United States Patent
Toizumi et al.

(10) Patent No.: US 8,590,372 B2
(45) Date of Patent: Nov. 26, 2013

(54) DEVICE AND METHOD FOR MEASURING TONER ADHESION

(75) Inventors: Kiyoshi Toizumi, Osaka (JP); Yasuhiro Shibai, Osaka (JP); Tadashi Nakamura, Osaka (JP)

(73) Assignee: Sharp Kabushiki Kaisha, Osaka-Shi (JP)

( * ) Notice: Subject to any disclaimer, the term of this patent is extended or adjusted under 35 U.S.C. 154(b) by 363 days.

(21) Appl. No.: 13/078,199

(22) Filed: Apr. 1, 2011

(65) Prior Publication Data

US 2011/0265561 A1 Nov. 3, 2011

(30) Foreign Application Priority Data

Apr. 30, 2010 (JP) ................. 2010-105664

(51) Int. Cl.
  *G01N 19/04* (2006.01)
(52) U.S. Cl.
  USPC ..................... 73/150 A
(58) Field of Classification Search
  USPC ..................... 73/150 A
  See application file for complete search history.

(56) References Cited

U.S. PATENT DOCUMENTS

| | | | |
|---|---|---|---|
| 2009/0197190 A1 | 8/2009 | Nakamura et al. | |
| 2009/0246675 A1 | 10/2009 | Nakamura et al. | |

FOREIGN PATENT DOCUMENTS

| | | | |
|---|---|---|---|
| CN | 101498904 A | | 8/2009 |
| JP | 61-266968 A | | 11/1986 |
| JP | 63263472 A | * | 10/1988 |
| JP | 10-267772 | | 10/1998 |
| JP | 11-153538 | | 6/1999 |
| JP | 11-237327 | | 8/1999 |
| JP | 11-258081 | | 9/1999 |
| JP | 2001-228075 | | 8/2001 |
| JP | 2003-98065 | | 4/2003 |
| JP | 2003-156426 | | 5/2003 |
| JP | 2005-201884 | | 7/2005 |
| JP | 2006-220472 | | 8/2006 |
| JP | 2007310275 | | 11/2007 |
| JP | 2008-310084 A | | 12/2008 |
| JP | 2009-175055 | | 8/2009 |

OTHER PUBLICATIONS

Inventor: Kikuta, Shinji et al., Title: Measuring Instrument for Electrostatic Charging Quantity Distribution of Toner, Date Published: Oct. 31, 1988, Page: Bibliographic data with Abstract for JP63263472(A).*

* cited by examiner

*Primary Examiner* — Lisa Caputo
*Assistant Examiner* — Roger Hernandez-Prewitt
(74) *Attorney, Agent, or Firm* — Nixon & Vanderhye P.C.

(57) ABSTRACT

A device for measuring adhesion of toner to carrier containing a magnetic component, the toner and the carrier being contained in a two-component developer, includes: a developer holding section including a first magnet for holding the two-component developer by a magnetic force; an airflow supply section for supplying airflow to the two-component developer held by the first magnet; a separated toner detecting section for detecting the number of toner separated from the carrier by the airflow; and an adhesion calculating section for calculating the adhesion of the toner to the carrier or an index of the adhesion, based on wind speed of the airflow and the detected number of the separated toner. Thus, the device can measure the adhesion of the toner to the carrier with high reproducibility and exactness.

9 Claims, 13 Drawing Sheets

| TONER | A | B | C |
|---|---|---|---|
| AVERAGE PARTICLE DIAMETER (μm) | 5.0 | 5.0 | 5.0 |
| AVERAGE PARTICLE DENSITY (kg/m³) | $1.2 \times 10^3$ | $1.2 \times 10^3$ | $1.2 \times 10^3$ |
| MATERIAL | POLYESTER | POLYESTER | POLYESTER |
| HOW TO PRODUCE | POLYMERIZATION | POLYMERIZATION | PULVERIZATION |
| SF-1 | 130 | 154 | 160 |
| SF-2 | 123 | 138 | 145 |

DEVICE AND METHOD FOR MEASURING TONER ADHESION

This Nonprovisional application claims priority under 35U.S.C. §119(a) on Patent Application No. 2010-105664 filed in Japan on Apr. 30, 2010, the entire contents of which are hereby incorporated by reference.

TECHNICAL FIELD

The present invention relates to a device and a method for measuring distribution of adhesion between toner and carrier contained in a two-component developer.

BACKGROUND ART

There have been known electrophotographic image forming apparatuses using a two-component developer containing toner and carrier having a magnetic component. Such image forming apparatuses are designed such that an electrostatic latent image corresponding to image data is formed on a surface of a photoreceptor and the electrostatic latent image is developed and made visible by toner. In this process, the two-component developer containing toner and carrier is carried to a position facing the surface of the photoreceptor, and the toner is transferred to the electrostatic latent image by an electrostatic attracting force which is exerted by the electrostatic latent image and which is stronger than adhesion (adhesive force) between the toner and the carrier.

It is known that in a developing process using the two-component developer, specific charge of toner, the shape of toner etc. have an influence on adhesion between toner and carrier. Further, it is known that the electrostatic property of toner deteriorates as time passes.

If the adhesion between toner and carrier drops, there occur inconveniences such as drop in image quality due to excessive amount of toner transferring from a developing device to a photoreceptor, and scattering of toner from the developing device.

As such, in view of development of toner for a two-component developer, optimization of toner for a developing process, evaluation of drop in toner quality etc., there has been requested a technique of easily and accurately measuring adhesion between toner and carrier or distribution of the adhesion therebetween.

In general, adhesion of powder such as toner is detected by measuring a strength required to separate the powder from a material to which the powder is attached. Known examples of a method for separating powder from a material include centrifugation, use of an electric field, and blowing.

In cases of centrifugation (see Patent Literatures 1-3 for example), there are provided a sample substrate which is positioned in a rotor of a centrifugal separator and to which powder is attached and a receiving substrate which is positioned to face the sample substrate and which receives powder separated from the sample substrate. Powder is separated from the sample substrate by a centrifugal force derived from rotation of the rotor and the powder is attached to the receiving substrate. Then, the mass of the powder attached to the receiving substrate is measured, the centrifugal force required is calculated based on the mass of the powder and the number of rotation of the rotor, and adhesion of the powder attaching to the sample substrate is calculated.

In cases of use of an electric field (see Patent Literatures 4-6 for example), there are provided a conductive sample substrate to which powder is attached and a conductive receiving substrate which is positioned to face the conductive sample substrate and which receives powder separated from the sample substrate. An electric field is applied across an electrode positioned at the sample substrate and an electrode positioned at the receiving substrate, so that charged powder is separated from the sample substrate and attached to the receiving substrate. Then, the mass of the powder attached to the receiving substrate is measured, and an electrostatic force required for the separation is calculated based on the measured mass, electrical charges of powder measured in advance, and the strength of the applied electric field. Thus, adhesion of powder attaching to the sample substrate is calculated.

In cases of blowing (see Patent Literature 2 for example), compressed air is jet at a predetermined speed toward a sample substrate to which powder is attached so that the powder is separated from the sample substrate, the separated powder is collected by a dust collector, air resistance of the powder is calculated based on a volume of the powder collected by the dust collector, and adhesion of powder attaching to the sample substrate is calculated based on the air resistance.

Further, Patent Literature 7 discloses that a sample substrate to which powder is attached is moved at a high speed so as to separate the powder from the sample substrate and adhesion of the powder attaching to the sample substrate is detected based on the number of particles and the mass of the particles just after the separation.

Further, Patent Literature 8 discloses that a developer made of a mixture of toner and carrier is magnetically attached to a sample substrate and the sample substrate is moved at a high speed in a direction perpendicular to a surface of the sample substrate while applying a predetermined electric field on the developer so that toner is separated from carrier, and the number of particles and a mass of the particles just after the separation are calculated so as to measure adhesion between toner and carrier.

CITATION LIST

Patent Literatures

[Patent Literature 1]
Japanese Patent Application Publication, Tokukaihei No. 10-267772 (published on Oct. 9, 1998)
[Patent Literature 2]
Japanese Patent Application Publication, Tokukaihei No. 11-237327 (published on Aug. 31, 1999)
[Patent Literature 3]
Japanese Patent Application Publication, Tokukaihei No. 11-258081 (published on Sep. 24, 1999)
[Patent Literature 4]
Japanese Patent Application Publication, Tokukaihei No. 11-153538 (published on Jun. 8, 1999)
[Patent Literature 5]
Japanese Patent Application Publication, Tokukai No. 2001-228075 (published on Aug. 24, 2001)
[Patent Literature 6]
Japanese Patent Application Publication, Tokukai No. 2005-201884 (published on Jul. 28, 2005)
[Patent Literature 7]
Japanese Patent Application Publication, Tokukai No. 2003-156426 (published on May 30, 2003)
[Patent Literature 8]
Japanese Patent Application Publication, Tokukai No. 2003-098065 (published on Apr. 3, 2003)

SUMMARY OF INVENTION

Technical Problem

However, although the methods disclosed in Patent Literatures 1-7 enable measuring adhesion between powder and a sample substrate, the methods do not enable measuring adhesion between toner and carrier. That is, in the methods disclosed in Patent Literatures 1-7, not only toner but also carrier are separated from the sample substrate and consequently it is difficult to measure adhesion between toner and carrier. Further, in the cases of blowing, it is difficult to direct airflow with uniform speed to individual toner in a developer and the airflow scatters not only toner but also carrier. This makes variations in the result of measurement, causing the measurement to have little reproducibility.

Further, although Patent Literature 8 describes detecting adhesion between toner and carrier, Patent Literature 8 describes that fine particles are separated from magnetic particles by shocking a sample substrate to which a developer is magnetically attached. Such separation causes variations in the force instantaneously applied on individual developers, resulting in low accuracy in measurement and low reproducibility.

An object of the present invention is to provide a device and a method each of which enables measuring adhesion between toner and carrier with high reproducibility and high accuracy.

Deterioration in electrostatic property of toner is not identical among individual toner in a developer, and there is individual difference. That is, a developer having been used for a long time contains toner whose electrostatic property has deteriorated greatly and toner whose electrostatic property has hardly deteriorated. Further, if there are variations in shape among individual toner, adhesion between toner and carrier may differ with respect to individual toner. Therefore, in order to evaluate the degree of deterioration in toner quality and characteristics of toner, it is necessary to grasp distribution of adhesion of individual toner. However, the technique disclosed in Patent Literature 8 enables obtaining only average adhesion of all toner contained in a developer, and does not enable detecting distribution of adhesion of individual toner.

Another object of the present invention is to provide a device and a method each of which enables measuring distribution of adhesion between toner and carrier with high reproducibility and high accuracy.

Solution to Problem

A device of the present invention for measuring toner adhesion is a device for measuring adhesion of toner to carrier containing a magnetic component, the toner and the carrier being contained in a two-component developer, the device comprising: a developer holding section including a first magnet for holding the two-component developer by a magnetic force; an airflow supply section for supplying airflow to the two-component developer held by the first magnet; a separated toner detecting section for detecting the number of toner separated from the carrier by the airflow; and an adhesion calculating section for calculating the adhesion of the toner to the carrier or an index of the adhesion, based on wind speed of the airflow and the detected number of the separated toner. The index is not particularly limited as long as the index indicates the degree of toner adhesion. Examples of the index include: the detected number of separated toner; and a wall shear force calculated based on the wind speed at which the number of the separated toner is detected.

Further, a method of the present invention for measuring toner adhesion is a method for measuring adhesion of toner to carrier containing a magnetic component, the toner and the carrier being contained in a two-component developer, the method comprising the steps of: causing a first magnet to hold the two-component developer by a magnetic force; supplying airflow to the two-component developer held by the first magnet; detecting the number of toner separated from the carrier by the airflow; and calculating the adhesion of the toner to the carrier or an index of the adhesion, based on wind speed of the airflow and the detected number of the separated toner.

Advantageous Effects of Invention

The device and the method for measuring toner adhesion can hold the two-component developer by a magnetic force generated by the first magnet, thereby holding the two-component developer in a magnetic brush-like manner. That is, the device and the method can hold the two-component developer in such a manner that the two-component developer stands perpendicularly to a surface of the first magnet which surface holds the two-component developer. Therefore, it is possible to cause the airflow to substantially evenly hit individual carrier and individual toner contained in the two-component developer. Therefore, by supplying the airflow to the two-component developer held by the first magnet, detecting the number of toner separated by the airflow, and calculating adhesion of toner to carrier or an index indicative of the toner adhesion, it is possible to measure the adhesion of toner to carrier or the index indicative of the toner adhesion with high reproducibility and exactness.

DESCRIPTION OF EMBODIMENTS (1. Configuration of Device 1 for Measuring Distribution of Toner Adhesion)

Figure 1:
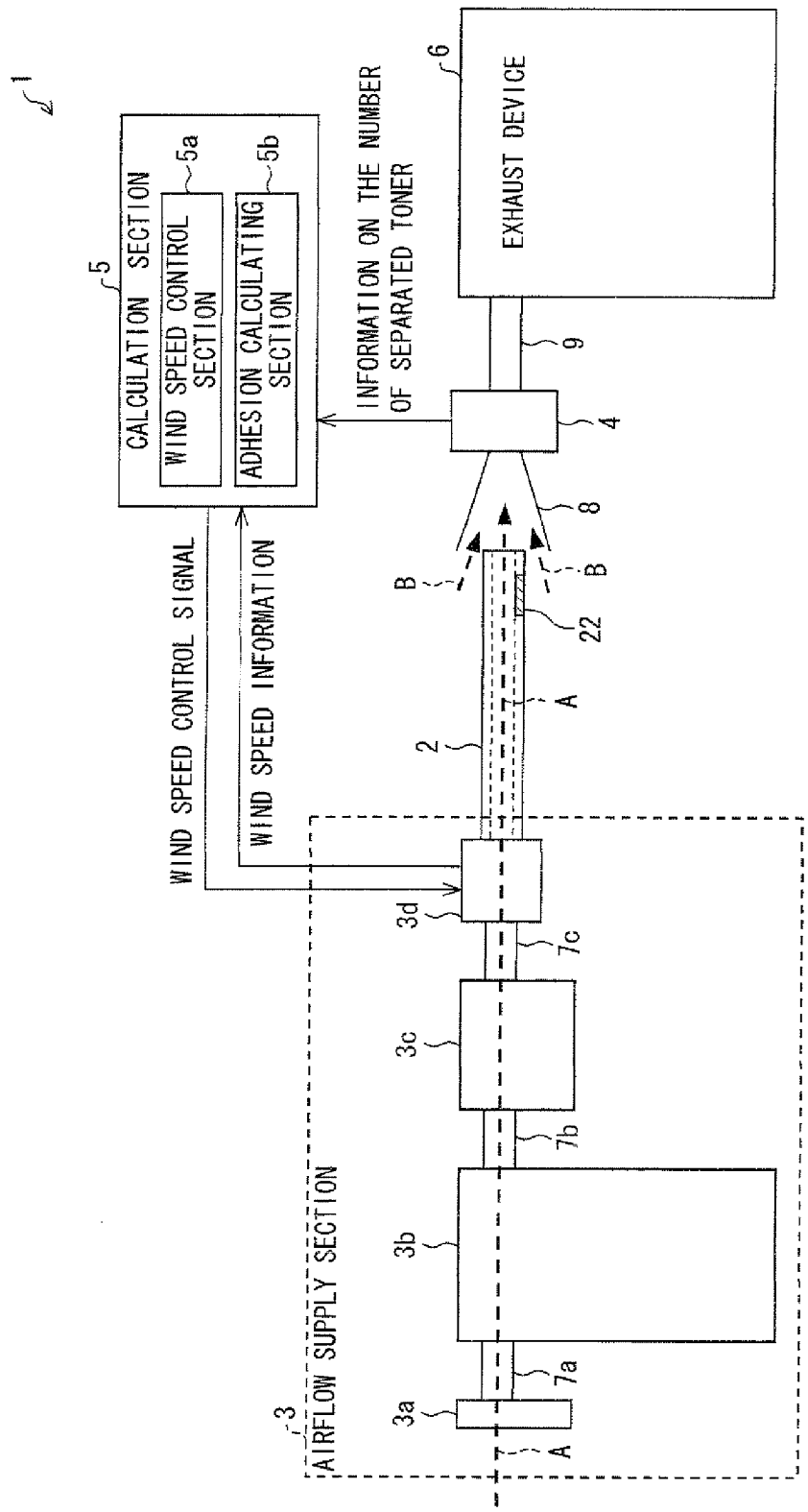
FIG. 1 is a block diagram showing a configuration of a device in accordance with one embodiment of the present invention for measuring distribution of toner adhesion.

An embodiment of the present invention is explained below. FIG. 1 is a block diagram showing a configuration of a device 1 in accordance with the present embodiment for measuring distribution of toner adhesion (device for measuring toner adhesion).

As shown in the drawing, the device 1 includes a developer holding section 2, an airflow supply section 3, a separated toner detecting section 4, a calculation section 5, and an exhaust device 6.

As shown in FIG. 1, the airflow supply section 3 includes a filter 3a, a compressor 3b, a drier 3c, and a wind speed regulator 3d. The filter 3a, the compressor 3b, the drier 3c, and the wind speed regulator 3d are connected with one another in this order via air pipes 7a, 7b, and 7c.

The filter 3a removes dusts etc. from air sucked in by the compressor 3b.

The compressor 3b sucks air in via the filter 3a and the air pipe 7a, compresses the sucked air, and sends the compressed air to the drier 3c via the air pipe 7b. The drier 3c dries the air sent from the compressor 3b via the air pipe 7b, and sends the dried air to the wind speed regulator 3d via the air pipe 7c. The wind speed regulator 3d is directly connected to an airflow guiding pipe 21 in the developer holding section 2. The wind speed regulator 3d regulates the speed of the air sent from the drier 3c via the air pipe 7c in accordance with an instruction (wind speed control signal) from a wind speed control section 5a of the calculation section 5, and sends the air with the regulated speed to the airflow guiding pipe 21. Further, the wind speed regulator 3d detects the speed of air sent to the airflow guiding pipe 21, and outputs wind speed information corresponding to the result of the detection to the calculation section 5 in real time. The wind speed regulator 3d is not particularly limited as long as it can regulate wind speed properly. An example of the wind speed regulator 3d is a combination of a normal airflow control valve and a normal wind meter.

Figure 2:
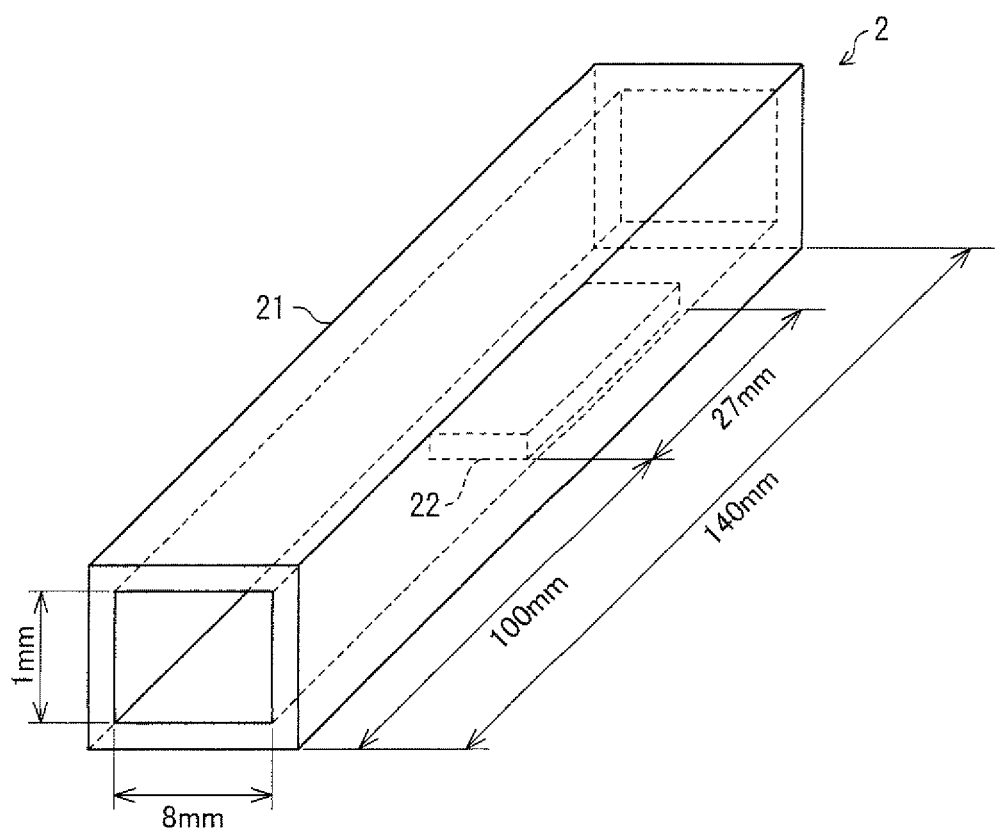
FIG. 2 is a perspective drawing showing a developer holding section included in the device shown in FIG. 1.
Figure 3:
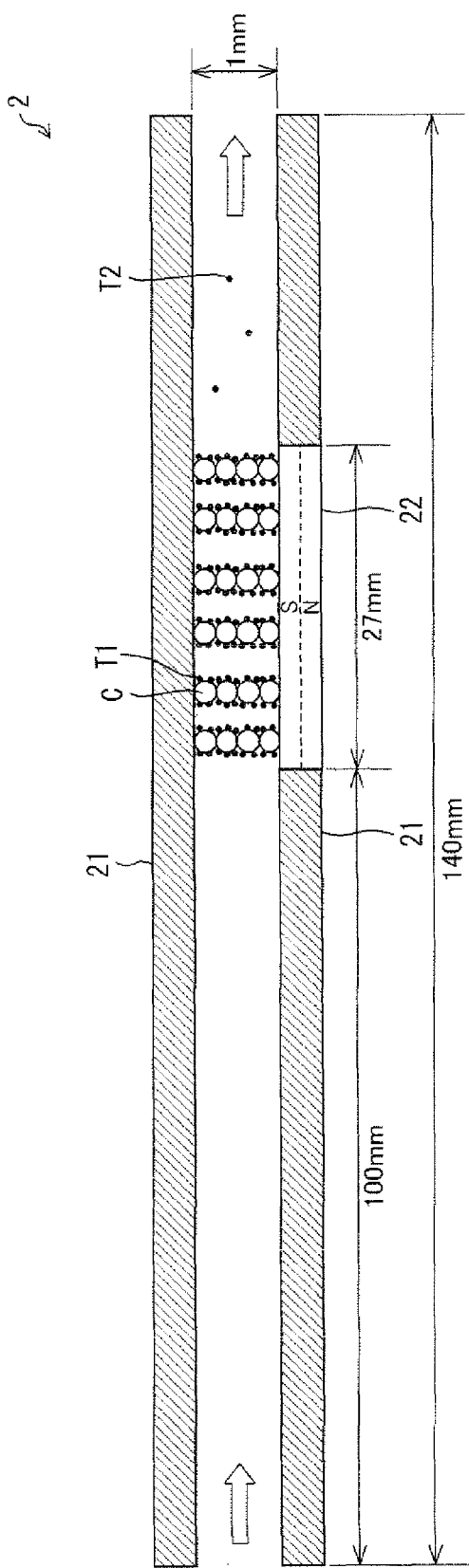
FIG. 3 is a cross sectional drawing showing the developer holding section included in the device shown in FIG. 1.

FIG. 2 is a perspective drawing showing the developer holding section 2. FIG. 3 is a cross sectional drawing showing the developer holding section 2. As shown in FIGS. 2 and 3, the developer holding section 2 includes the airflow guiding pipe 21 made of a hollow and square pillar-shaped pipe and a first magnet 22 positioned on an inner wall of the airflow guiding pipe 21.

The airflow guiding pipe 21 used in the present embodiment is designed such that its length is 140 mm and an inner wall of its cross section perpendicular to a direction in which the airflow pipe 21 extends has a rectangular shape whose width (width of airflow path) is 8 mm and whose height (height of airflow path) is 1 mm. The shape and the size of the airflow guiding pipe 21 are not limited to these.

The first magnet 22 is positioned on the inside surface of the airflow guiding pipe 21 in such a manner that a surface of the first magnet 22 which surface is closer to the inside of the airflow guiding pipe 21 exists on the same plane as the inside surface of the airflow guiding pipe 21 other than an area where the first magnet 22 is positioned. Further, the first magnet 22 is positioned in such a manner that the south pole thereof is closer to the inside of the airflow guiding pipe 21 and the north pole thereof is closer to the outside of the airflow guiding pipe 21. Consequently, a radial magnetic field is generated between the south pole and the north pole of the first magnet 22, and a two-component developer consisting of toner T1 and carrier C containing a magnetic component is held in a magnetic brush-like manner by the first magnet 22, as schematically shown in FIG. 3 (held in such a manner that the two-component developer stands on the surface of the first magnet 22 in a vertical direction).

In the present embodiment, the first magnet 22 is a permanent magnet designed such that the surface thereof closer to the inside of the airflow guiding pipe 21 has a rectangular shape with a width of 8 mm and a length of 27 mm and magnetic flux density is 120 mT. However, the design of the first magnet 22 is not limited to this. In the present embodiment, the first magnet 22 is positioned in such a manner that the south pole thereof is closer to the inside of the airflow guiding pipe 21 and the north pole thereof is closer to the outside of the airflow guiding pipe 21. Alternatively, the first magnet 22 may be positioned in such a manner that the north pole thereof is closer to the inside of the airflow guiding pipe 21 and the south pole thereof is closer to the outside of the airflow guiding pipe 21.

The separated toner detecting section 4 detects the number of separated toner T2 which is separated from the carrier of the two-component developer held by the first magnet 22 and which is conveyed together with airflow, and outputs information indicative of the detected number to the calculation section 5 in real time. The separated toner detecting section 4 is not particularly limited as long as it can detect the number of toner contained in the airflow. An example of the separated toner detecting section 4 is a commercially available particle analyzer. In the present embodiment, the separated toner detecting section 4 is a laser dust monitor (particle analyzer) LD-1 manufactured by sibata scientific technology ltd.

As shown in FIG. 1, the separated toner detecting section 4 is connected with an airflow guiding pipe 8 having a conical shape designed such that a cross section of an opening of the airflow guiding pipe 8 is larger as the cross section is closer to the developer holding section 2. The airflow guiding pipe 8 sucks in an airflow A exhausted from the airflow guiding pipe 21 of the developer holding section 2 and an airflow B coming from the peripherals of the airflow guiding pipe 21. Since the airflow guiding pipe 8 sucks in not only the airflow A but also the airflow B coming from the peripherals of the airflow guiding pipe 21, it is possible to prevent the separated toner T2 from attaching to the walls of the airflow guiding pipe 8, thereby improving detection accuracy.

The exhaust device 6 includes a filter for separating the separated toner T2 from air and an air suction device (both are not shown), and is connected with the separated toner detecting section 4 via an exhaust pipe 9. Consequently, air exhausted from the separated toner detecting section 4 is sucked in by the air suction device, the separated toner T2 contained in the sucked air is separated from the air by the filter, and the air from which the separated toner T2 is separated is exhausted to the outside.

The calculation section 5 includes a wind speed control section 5a and an adhesion calculating section 5b. In accordance with wind speed information inputted from the wind speed regulator 3d of the airflow supply section 3, the wind speed control section 5a carries out a feedback control of the wind speed regulator 3d so that the speed of airflow supplied from the wind speed regulator 3d to the airflow guiding pipe 21 has a target value. The adhesion calculating section 5b calculates adhesion of toner to carrier (distribution of toner adhesion), based on the wind speed information inputted from the wind speed regulator 3d and the information indicative of the number of the separated toner T2 which is inputted from the separated toner detecting section 4.

(2. Result of Test)

The following explains the result of measurement of toner adhesion (the result of detection of distribution of toner adhesion), which was carried out using the device 1 for measuring distribution of toner adhesion.

Figures 4, 5:
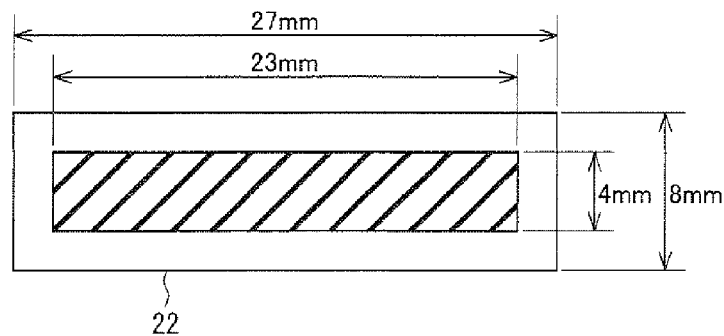
FIG. 4 is a plane drawing showing a first magnet included in the developer holding section shown in FIGS. 2 and 3.
FIG. 5 is an explanatory drawing showing properties of toner used in a test.

The test was carried out as follows: initially, a two-component developer consisting of toner and carrier was mixed and stirred so that the toner was charged, and the two-component developer was held by the first magnet 22 of the developer holding section 2. In the present embodiment, as shown in FIG. 4, the developer was held only at a central portion of the upper surface of the first magnet 22 (a holding surface which holds the two-component developer). The purposes of this configuration are (i) reducing an influence of airflow disturbed by the wall of the airflow guiding pipe 21 on the result of the measurement and (ii) holding the developer only at a region where lines of the magnetic force of the first magnet 22 are substantially perpendicular to the holding surface which holds the two-component developer, so that the two-component developer is held in a magnetic brush-like manner and airflow is evenly directed to individual carrier and individual toner. That is, since it is difficult to hold the two-component developer in a magnetic brush-like manner at peripherals of the first magnet 22 where lines of the magnetic force and the holding surface which holds the two-component developer form a small angle, the present embodiment is designed such that the two-component developer is held only at the central portion of the upper surface of the first magnet 22 so that the two-component developer to be measured is held evenly in a magnetic brush-like manner.

Specifically, the peripherals on the upper surface of the first magnet 22 were masked with a non-magnetic film, and 20 mg of a mixed and stirred two-component developer was dispersed by a sieve and was made fall by gravity onto a region with a width of 4 mm, a length of 23 mm, and an area of 92 mm$^2$ (hatched portion in FIG. 4) positioned on the central portion of the upper surface of the first magnet 22. Accordingly, the amount of the developer per unit area is 0.22 mg/mm$^2$=0.22 kg/m$^2$. The sieve used here has 200 meshes each with the size 75 µm. Since the first magnet 22 is ferromagnetic and carrier contains a magnetic component, the two-component developer fallen onto the first magnet 22 stood in a magnetic brush-like manner (stood perpendicularly to the surface of the first magnet 22). Thereafter, the non-magnetic film used for the masking was peeled off, and the first magnet 22 holding the two-component developer was set in the developer holding section 2.

Subsequently, airflow was begun to be supplied from the airflow supply section 3 to the airflow guiding pipe 21, and the wind speed was increased at a predetermined rate (increased monotonously) so that the wind speed reached 150 m/s after a predetermined time.

Consequently, toner T1 attaching to carrier C in the developer holding section 2 was subjected to air resistance according to the wind speed. When the air resistance to which the toner T1 was subjected got larger than the adhesion between the toner T1 and the carrier C, the toner T1 was separated from the carrier C to become the separated toner T2, which was carried to the separated toner detecting section 4 by airflow.

In the test, detection of the distribution of the toner adhesion was carried out with respect to each of toner A-C shown in FIG. 5. The toner A was made of polyester produced by polymerization, with an average particle diameter of 5.0 µm, an average particle density of 1.2×10$^3$ kg/m$^3$, SF-1 of 130, and SF-2 of 123. The toner B was made of polyester produced by polymerization, with an average particle diameter of 5.0 µm, an average particle density of 1.2<10$^3$ kg/m$^3$, SF-1 of 154, and SF-2 of 138. The toner C was made of polyester produced by pulverization, with an average particle diameter of 5.0 µm, an average particle density of 1.2×10$^3$ kg/m$^3$, SF-1 of 160, and SF-2 of 145. SF-1 and SF-2 are shape factors indicative of the shape of a toner particle, and the shape factors closer to 100 indicate a particle shape closer to a sphere. Specifically, SF-1 and SF-2 are represented by the following equations:

$$SF-1 = \frac{\pi L_{max}}{4} \times \frac{100}{\text{Area}}$$

$$SF-2 = \frac{L_{perimeter}}{4\pi} \times \frac{100}{\text{Area}}$$

where $L_{max}$ represents the absolute maximum length of a toner particle, Area represents a projected area of the toner particle, and $L_{perimeter}$ represents a perimeter of the toner particle.

The carrier used here was obtained by coating ferrite core particles with resin and had an average particle diameter of 45-50 µm.

Figure 6:
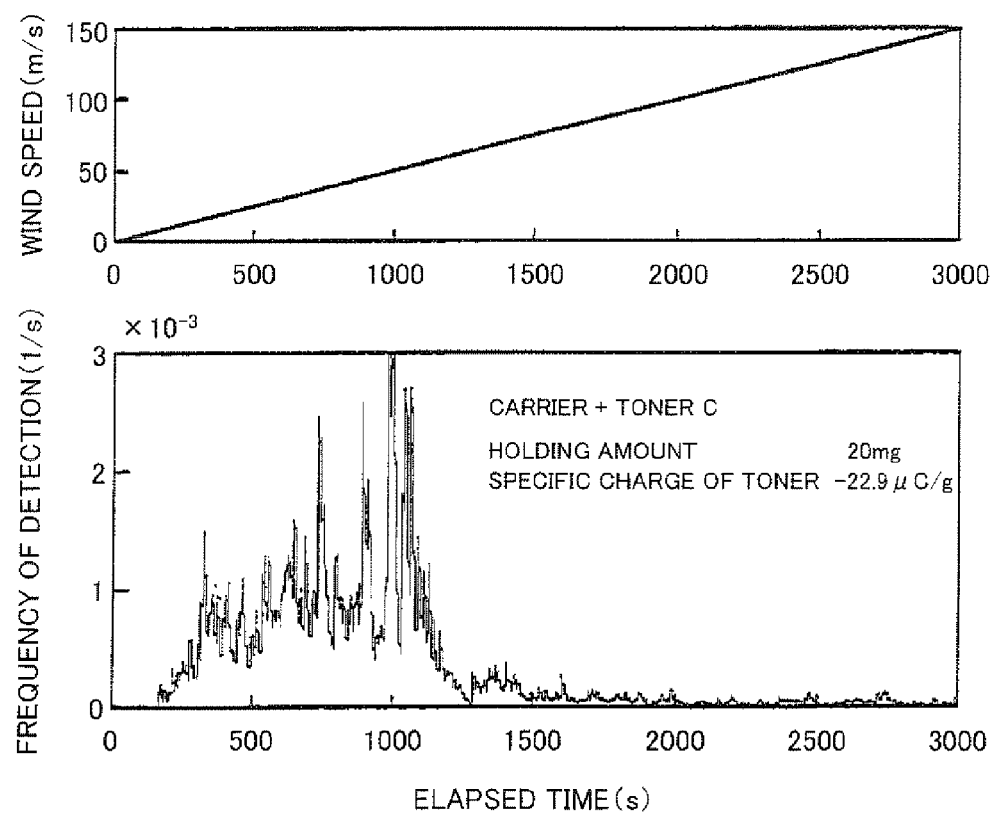
FIG. 6 is a graph showing an example of the result of a test using the device shown in FIG. 1, showing frequency of detecting separated toner per elapsed time, in a case where wind speed was increased at a predetermined rate.

FIG. 6 is a graph showing frequency of detecting separated toner per elapsed time, in a case where the wind speed was increased at a predetermined rate (acceleration of airflow α=0.05 m/s$^2$) so that the wind speed reached 150 m/s 50 min after the start of supply of the airflow. The upper graph of FIG. 6 shows a change per time in the wind speed, and the lower graph shows frequency distribution (dispersion profile) of the number of separated particles.

Figure 7:
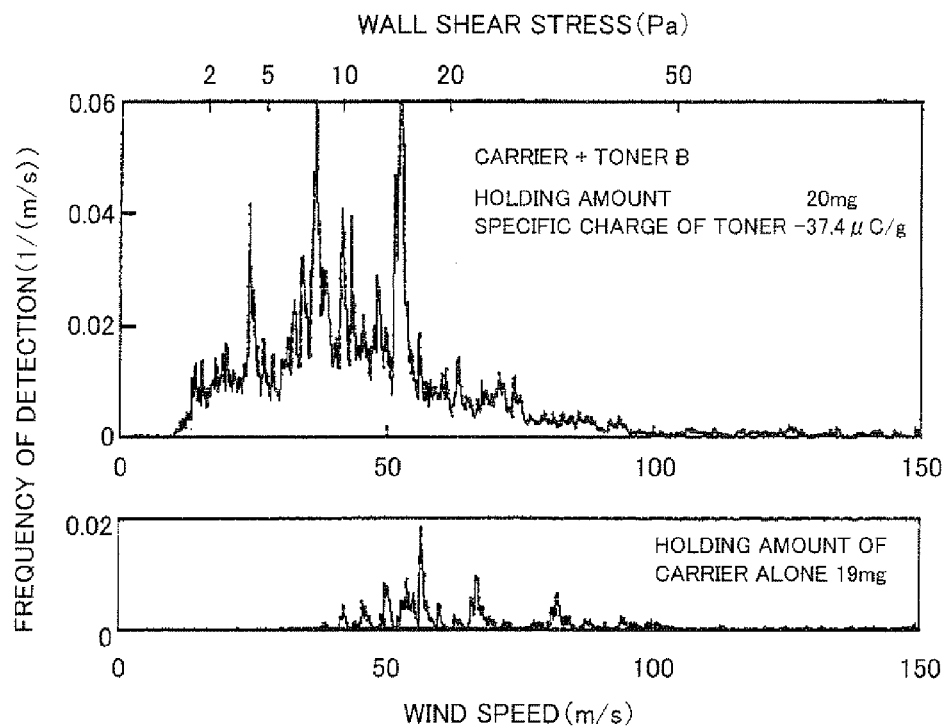
FIG. 7 is a graph showing an example of the result of a test using the device shown in FIG. 1. The upper graph of FIG. 7 shows frequency of detecting separated toner per elapsed time, in a case where wind speed was increased at a predetermined rate. The lower graph of FIG. 7 shows frequency of detecting carrier alone per elapsed time, in a case wind speed was increased at a predetermined rate.

The upper graph of FIG. 7 shows frequency of detecting separated toner per elapsed time, in a case where the wind speed was increased at a predetermined rate (acceleration of airflow α=0.5 m/s$^2$) so that the wind speed reached 150 m/s 5 min after the start of supply of the airflow. The lower graph of FIG. 7 shows frequency of detecting carrier per elapsed time, in a case where 19 mg of carrier alone which was not mixed with toner was attached to the central portion of the upper surface of the first magnet 22 and the wind speed was increased at a predetermined rate (acceleration of airflow α=0.5 m/s$^2$) so that the wind speed reached 150 m/s 5 min after the start of supply of the airflow. The longitudinal and lateral axes in the lower graph are based on the same units as those of the upper graph, respectively, in order to facilitate comparison of the lower graph with the upper graph. As is evident from FIG. 7, the number of dispersed carrier was very small compared with the number of dispersed toner separated from carrier. As is seen from the upper graph of FIG. 7, the dispersion profile is hardly influenced by dispersion of carrier, and is dominantly influenced by dispersion of toner particles. In order to confirm consistency between the result shown in FIG. 7 and the actual phenomenon, observation with a microscope was carried out. As a result of the observation, in a range of the wind speed being 0-40 m/s, no dispersion of carrier was seen and only dispersion of toner was seen.

Figure 8:
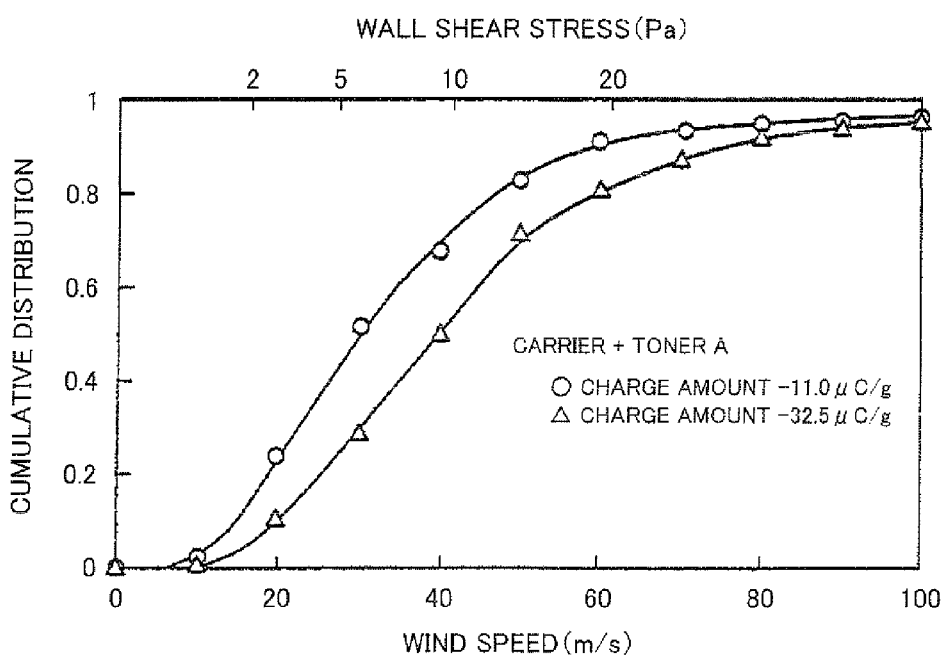
FIG. 8 is a graph showing an example of the result of a test using the device shown in FIG. 1, showing cumulative distribution of the number of detecting separated toner in a case where wind speed was increased at a predetermined rate.

FIG. 8 is a graph showing cumulative distribution of the number of detecting separated toner (toner adhesion) in a case where the toner A charged with—11.0 µC/g and the toner A charged with—32.5 µC/g were used and the wind speed was increased at a predetermined rate (acceleration of airflow α=0.5 m/s$^2$) so that the wind speed reached 150 m/s 5 min after the start of supply of the airflow.

The cumulative distribution was obtained in such a manner that the adhesion calculating section 5b extracts the number of detecting separated toner with respect to each wind speed ranging from 0-150 m/s, cumulates the number of separated toner up to 150 m/s, divides the number of detecting separated toner with respect to each wind speed by the cumulated number, and cumulates the number obtained by the division with respect to each wind speed ranging from 0-150 m/s.

The strength applied on toner by the airflow gets larger in proportion to the power of the wind speed. Accordingly, the adhesion calculating section 5b calculates cumulative distribution of toner adhesion (distribution of toner adhesion) based on the cumulative distribution of the number of detecting the separated toner with respect to each wind speed.

Figure 9:
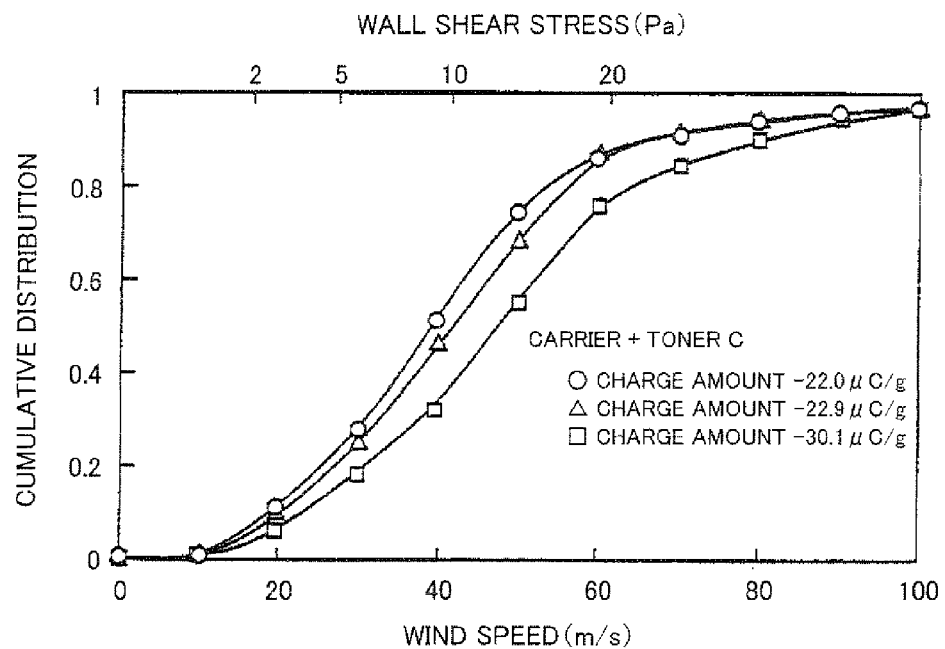
FIG. 9 is a graph showing an example of the result of a test using the device shown in FIG. 1, showing cumulative distribution of the number of detecting separated toner in a case where wind speed was increased at a predetermined rate.

FIG. 9 is a graph showing cumulative distribution of the number of detecting separated toner (toner adhesion) in a case where the toner C charged with—22.0 µC/g, the toner C charged with—22.9 µC/g, and the toner C charged with—30.1 µC/g were used and the wind speed was increased at a predetermined rate (acceleration of airflow α=0.5 m/s$^2$) so that the wind speed reached 150 m/s 5 min after the start of supply of the airflow.

Figure 10:
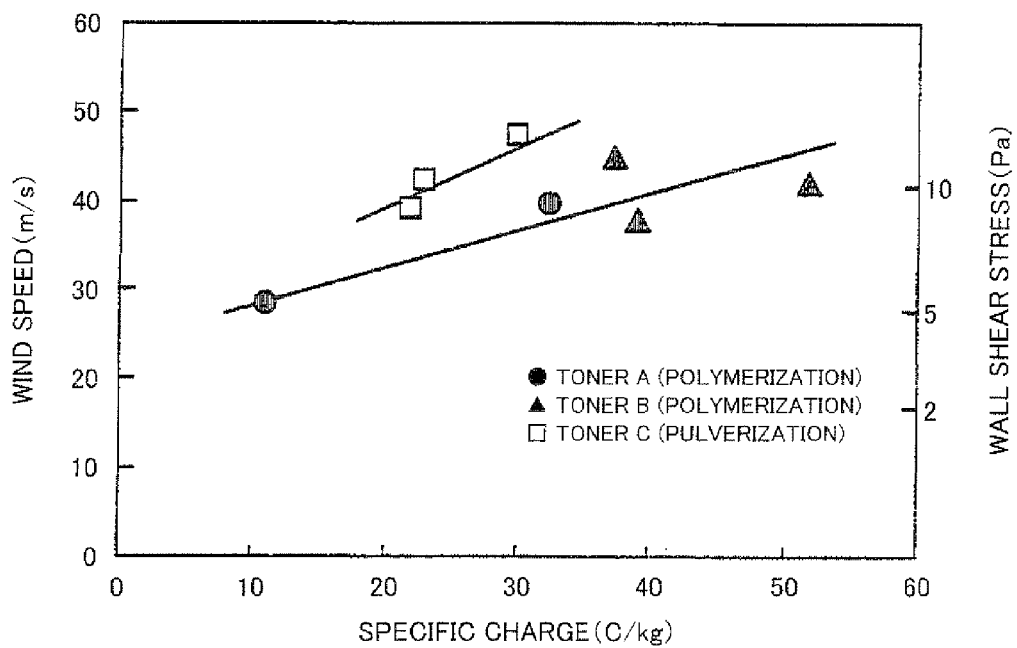
FIG. 10 is a graph showing an example of the result of a test using the device shown in FIG. 1, the graph plotting wind speed at which 50% of toner in a two-component developer was separated from carrier, with respect to each of plural kinds of toner with different specific charges.

FIG. 10 is a graph of plotting the wind speed at which 50% of toner was separated from carrier in cases where the wind speed was increased at a predetermined rate (acceleration of airflow α=0.5 m/s$^2$) so that the wind speed reached 150 m/s 5 min after the start of supply of the airflow with respect to each of the toner A-C with different specific charges.

As shown in FIGS. 8 and 9, the device 1 for measuring distribution of toner adhesion in accordance with the present embodiment enabled accurately detecting the relation between a specific charge of toner and adhesion of toner to carrier. That is, it is known that in general, toner with a larger specific charge has larger adhesion to carrier as is evident from FIG. 10, and detection by the device 1 in accordance with the present embodiment accurately confirmed this fact. As shown in FIG. 10, the toner produced by pulverization has larger adhesion to carrier than the toner produced by polymerization.

The following explains the result of a test in which distribution of adhesion was measured both by the device 1 in accordance with the present embodiment and by a device for measuring distribution of toner adhesion in accordance with a Comparative Example in which a developer was positioned inside the airflow guiding pipe 21 without being held by the first magnet 22.

Figure 11:
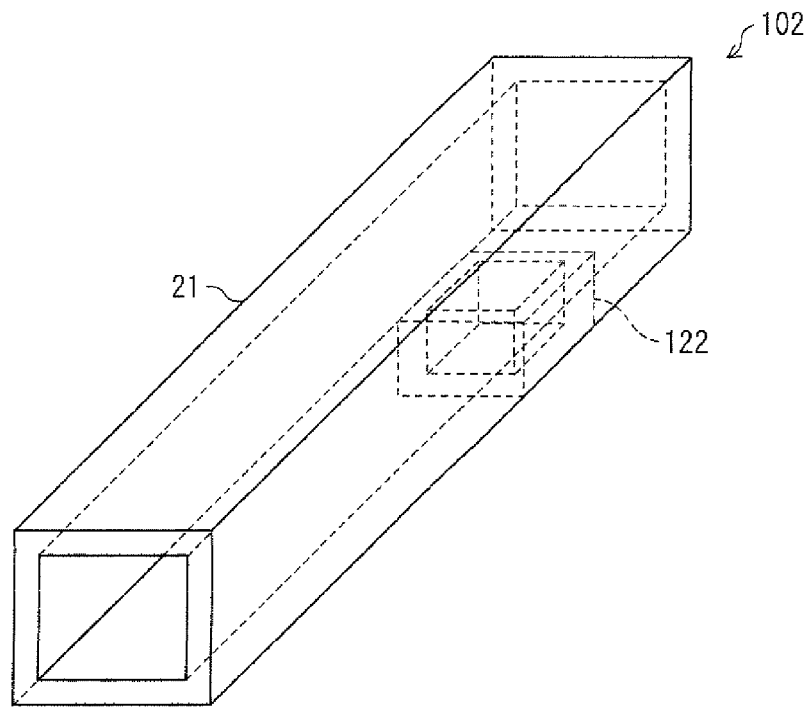
FIG. 11 is a perspective drawing showing a developer holding section in accordance with a Comparative Example.
Figure 12:
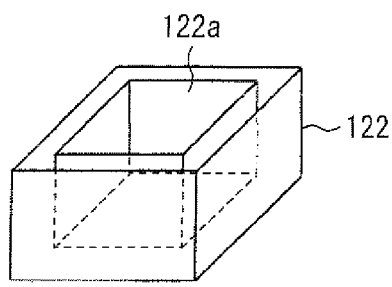
FIG. 12 is a perspective drawing showing a developer container included in the developer holding section shown in FIG. 11.

FIG. 11 is a perspective drawing showing a developer holding section 102 in accordance with the Comparative Example. FIG. 12 is a perspective drawing showing a developer container 122 included in the developer holding section 102. The device for measuring toner adhesion in accordance with the Comparative Example is the same as the device 1 except for the structure of the developer holding section. As shown in FIG. 11, the developer holding section 102 includes the developer container 122 instead of the first magnet 22 in the developer holding section 2. As shown in FIG. 12, the developer container 122 has a recess 122a having a rectangular parallelepiped shape with a width of 4 mm and a length of 23 mm. A developer is contained in the recess 122a.

Figure 13:
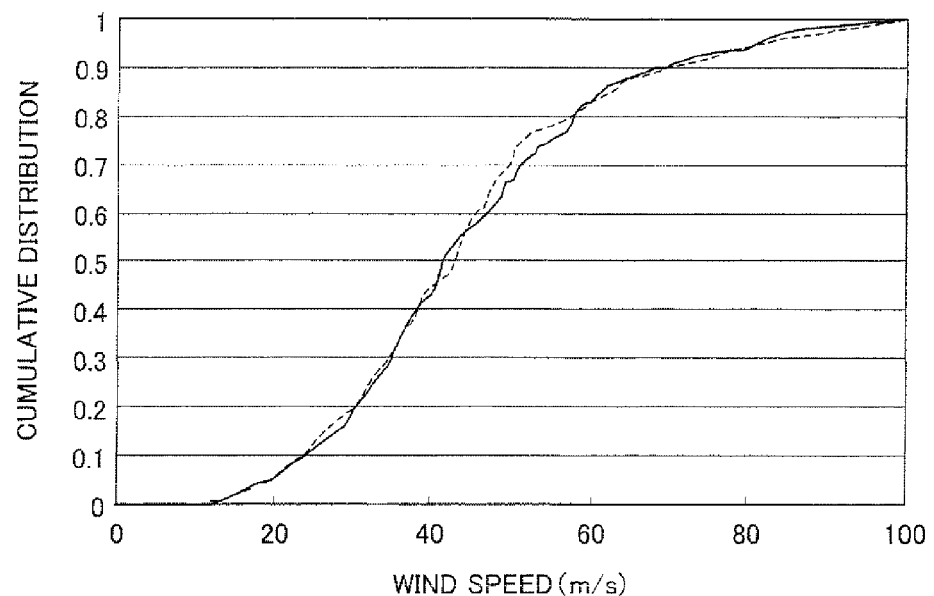
FIG. 13 is a graph showing an example of the two results of tests carried out with the device shown in FIG. 1 under the same condition, the two results being cumulative distributions of the number of detecting separated toner per elapsed time in a case where wind speed was increased at a predetermined rate with respect to an elapsed time.

FIG. 13 is a graph showing the two results of cumulative distributions carried out by the device 1 in accordance with the present embodiment under the same condition. Each cumulative distribution was a cumulative distribution of the number of detecting separated toner (toner adhesion) in a case where amorphous toner (pulverized toner) charged with—22.0 µC/g was used and wind speed was increased with a predetermined rate (acceleration of airflow α=0.5 m/s$^2$) so that the wind speed reached 150 m/s 5 min after the start of supply of the airflow.

Figure 14:
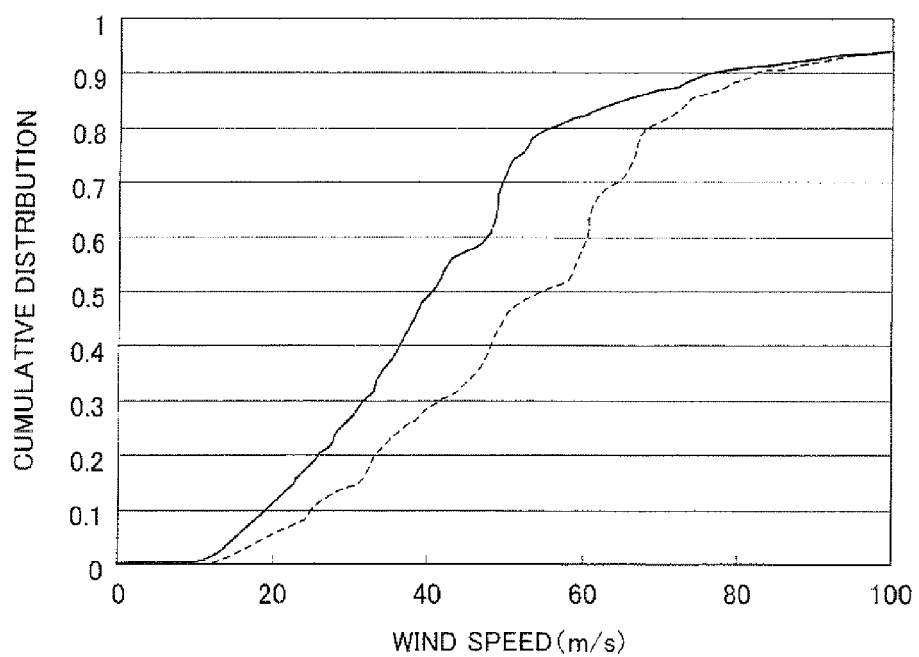
FIG. 14 is a graph showing an example of the two results of tests carried out with the device shown in FIG. 11 in accordance with the Comparative Example under the same condition, the two results being cumulative distributions of the number of detecting separated toner per elapsed time in a case where wind speed was increased at a predetermined rate with respect to an elapsed time.

FIG. 14 is a graph showing the two results of cumulative distributions carried out by the device in accordance with the Comparative Example under the same condition as in the case of FIG. 13 except for the developer container. Each cumulative distribution is a distribution of the number of detecting separated toner (toner adhesion).

As shown in FIG. 14, in a case where the device in accordance with the Comparative Example was used, the result varied greatly with respect to each measurement and reproducibility of the result of the measurement was low. In contrast thereto, as shown in FIG. 13, in a case where the device 1 in accordance with the present embodiment was used, substantially the same result was obtained with respect to each measurement, and reproducibility of the result of the measurement was high.

This seems to be because in the device in accordance with the Comparative Example, (1) airflow hits only the upper surface of the developer contained in the developer container 122 and does not evenly hit the developer and (2) carrier which is not held by a magnet is dispersed by the airflow.

In contrast thereto, the device 1 in accordance with the present embodiment is designed such that (1) the developer is held by the first magnet 22 in a magnetic brush-like manner (in such a manner that the developer stands perpendicularly to the surface of the first magnet 22) so that the airflow evenly hits the developer and (2) carrier containing a magnetic component is magnetically held by a magnetic field of the first magnet 22 so that the carrier is not dispersed by the airflow and only toner separated from the carrier is dispersed. Such design seems to allow the device 1 to obtain the result of the measurement with high reproducibility.

As described above, the device of the present invention for measuring distribution of adhesion of toner to carrier includes: the developer holding section 2 including the first magnet 22 for holding the two-component developer by a magnetic force; the airflow supply section 3 for supplying airflow to the two-component developer held by the first magnet 22; the separated toner detecting section 4 for detecting the number of toner separated from the carrier by the airflow; and the adhesion calculating section 5b for calculating distribution of the adhesion of the toner to the carrier, based on wind speed of the airflow and the number of the separated toner detected by the separated toner detecting section 4.

As described above, by causing the first magnet 22 to hold the two-component developer by a magnetic force, it is possible to hold the two-component developer in a magnetic brush-like manner. This enables the airflow to substantially evenly hit individual carrier and toner contained in the two-component developer. Thus, the airflow is supplied to the two-component developer held by the first magnet 22, the number of toner separated from the carrier by the airflow is detected, and distribution of the adhesion of the toner to the carrier is calculated based on wind speed of the airflow and the detected number of the separated toner. This enables measuring the distribution of the adhesion of the toner to the carrier with high reproducibility and exactness.

In the present embodiment, an explanation was made as to a case where the wind speed control section 5a changes the wind speed of the airflow supplied from the airflow supply section 3 to the airflow guiding pipe 21, and the adhesion calculating section 5b calculates distribution of toner adhesion based on the detected number of separated toner with respect to each wind speed. However, the present invention is not limited to this case. For example, the present invention may be arranged such that the wind speed of the airflow supplied from the airflow supply section 3 to the airflow guiding pipe 21 is set to be a certain value, and average adhesion of whole toner contained in a developer is calculated based on the detected number of separated toner at the wind speed thus set. The present invention may also be arranged such that the wind speed control section 5a calculates average adhesion of toner contained in a developer based on the calculated distribution of toner adhesion.

Instead of calculating adhesion or distribution of adhesion, an index indicative of the degree of adhesion or distribution of an index indicative of the degree of adhesion may be calculated. Examples of the index include: the detected number of separated toner; a value obtained by dividing the detected number of separated toner by sampling cycle etc. of the separated toner; and a wall shear force calculated based on the wind speed at which the number of the separated toner is detected.

In the present embodiment, the first magnet 22 is a permanent magnet with magnetic flux density of 120 mT. The present invention is not limited to this, and may have any configuration as long as the configuration generates a magnetic field which is strong enough to prevent carrier from being separated from the first magnet 22 by the airflow from the airflow supply section 3 (alternatively, a magnetic field strong enough to restrict the amount of carrier separated from the first magnet 22 to a range which does not has an influence on the result of the measurement of the separated toner T2).

Further, in the present embodiment, only one first magnet 22 is provided at the bottom surface of the airflow guiding pipe 21 in the developer holding section 2. However, the present invention is not limited to this configuration.

Figure 15:
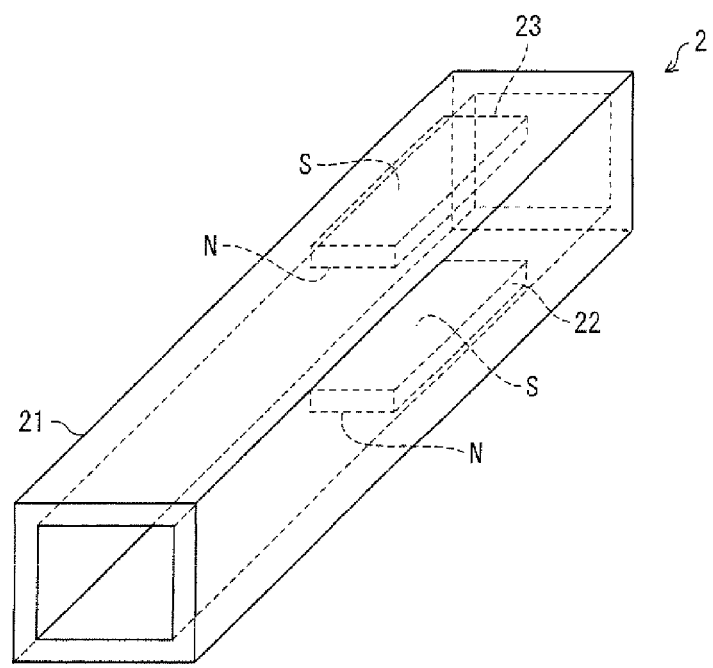
FIG. 15(a) is a perspective drawing showing a modification example of the developer holding section included in the device shown in FIG. 1.
FIG. 15(b) is an enlarged perspective drawing showing a first magnet and a second magnet which are provided in the developer holding section shown in FIG. 15(a).
Figure 15:
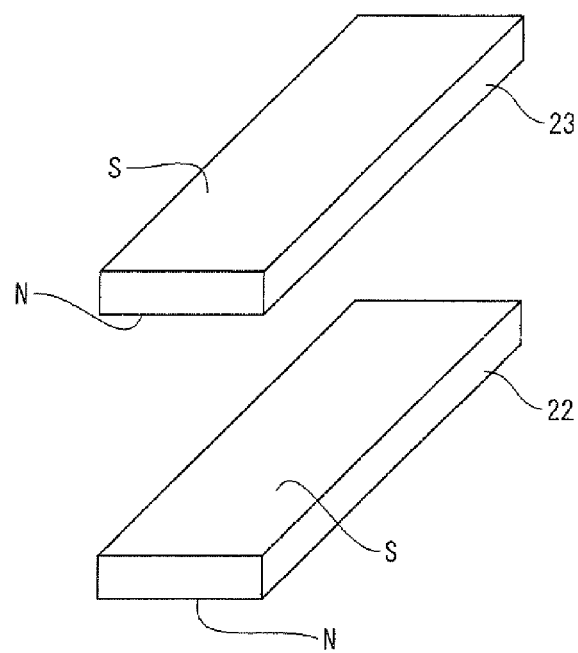
Figure 16:
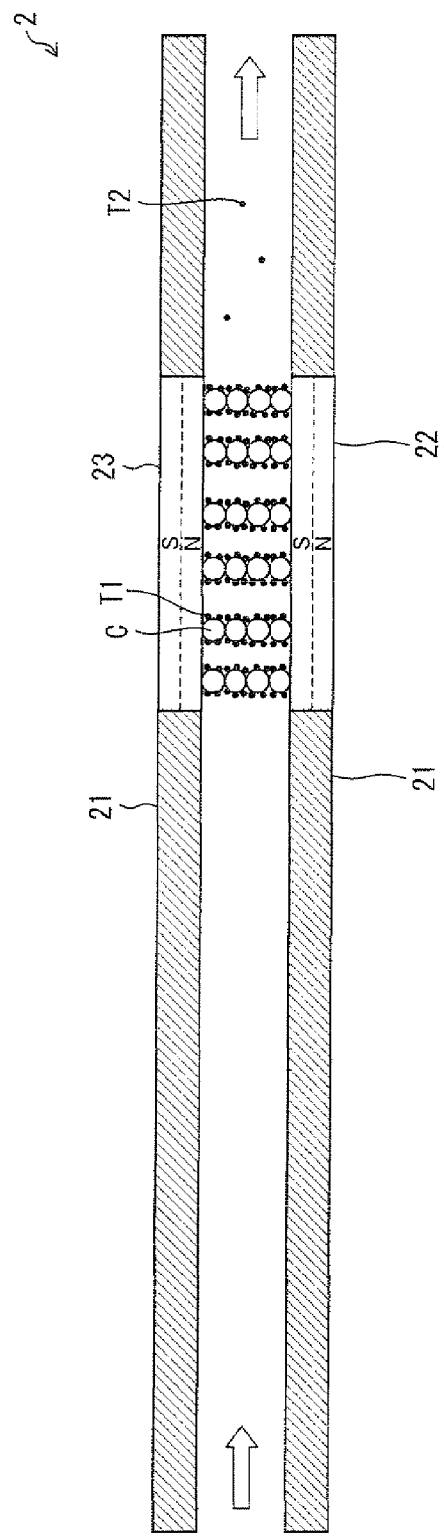
FIG. 16 is a cross sectional drawing showing a modification example of the developer holding section included in the device shown in FIG. 1.

FIG. 15(a) is a perspective drawing showing a modification example of the developer holding section 2. FIG. 15(b) is an enlarged perspective drawing showing a first magnet 22 and a second magnet 23 which are provided in the developer holding section 2 in accordance with the present modification example. FIG. 16 is a cross sectional drawing showing the developer holding section 2 in accordance with the present modification example.

As shown in these drawings, the second magnet 23 may be provided on the upper surface of the inside wall of the airflow guiding pipe 21 in such a manner that the second magnet 23 is positioned on a part facing the first magnet 22 and a surface of the second magnet 23 which surface facing the first magnet 22 is a north pole (has a polarity opposite to that of a surface of the first magnet 22 which surface faces the second magnet 23). This configuration generates substantially parallel magnetic fields between the first magnet 22 and the second magnet 23, thereby holding a two-component developer consisting of toner and carrier containing a magnetic component in a magnetic brush-like manner (in such a manner that the two-component developer stands perpendicularly to the front surfaces of the first magnet 22 and the second magnet 23).

Figure 17:
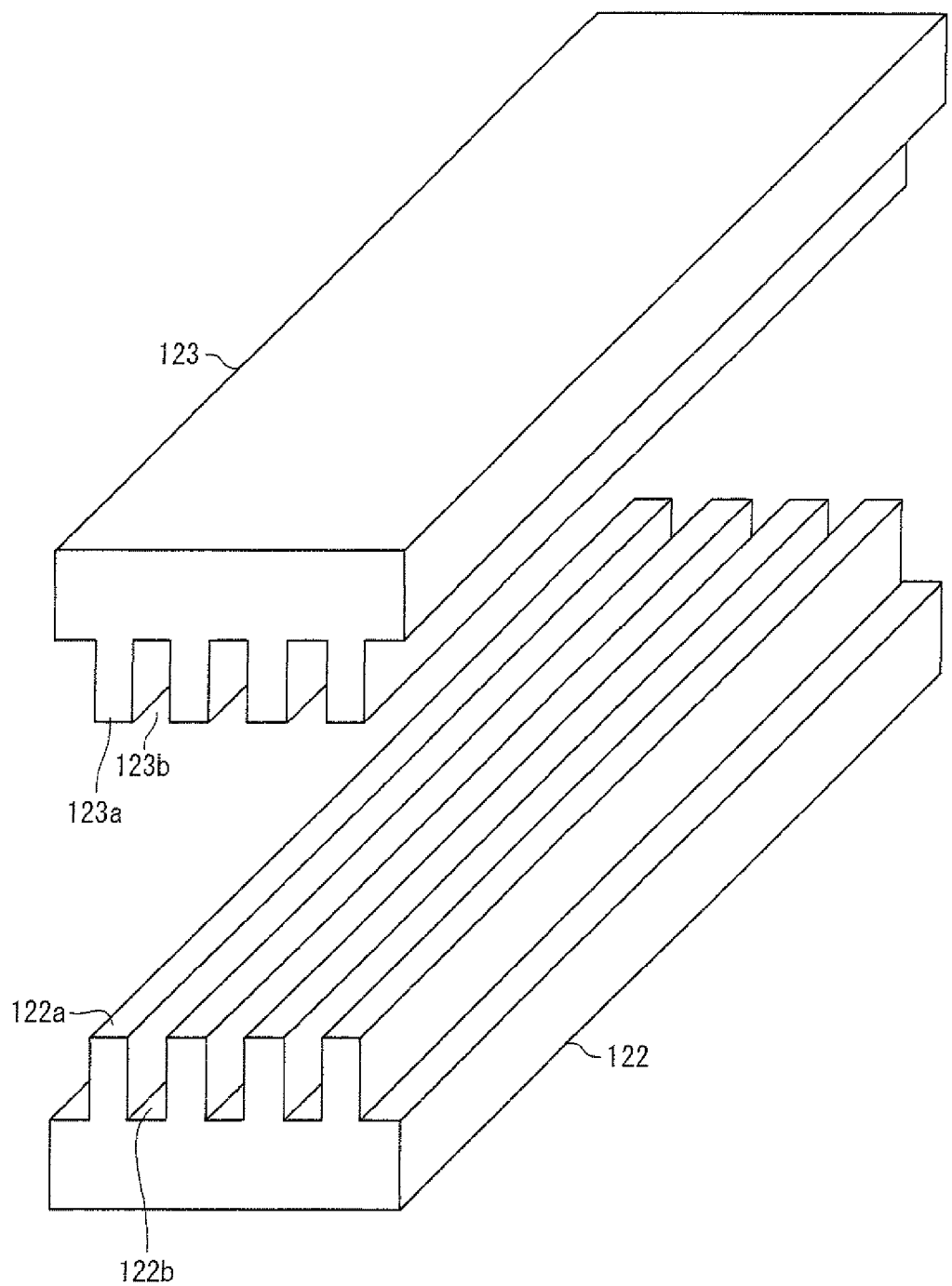
FIG. 17 is a perspective drawing showing a modification example of the first magnet and the second magnet which are shown in FIGS. 15(a) and 15(b) and which are included in the device for measuring distribution of toner adhesion.

FIG. 17 is a perspective drawing showing a modification example of the first magnet 22 and the second magnet 23 provided in the developer holding section 2. In the example shown in the drawing, a surface of the first magnet 122 which surface faces the second magnet 123 is provided with (i) a plurality of convex portions (first protrusions) 122a protruding toward the second magnet 123 and (ii) a plurality of concave portions (slits) 122b which are recessed in a direction away from the second magnet 123. Further, a surface of the second magnet 123 which surface faces the first magnet 122 is provided with (i) a plurality of convex portions (second protrusions) 123a protruding toward the first magnet 122 in such a manner that the convex portions 123a face the convex portions 122a of the first magnet 122, respectively, and (ii) a plurality of concave portions (slits) 123b recessed in a direction away from the first magnet 122 in such a manner that the concave portions 123b face the concave portions 122b of the first magnet 122, respectively. Further, each of the convex portions 122a and the convex portions 123a has an elongated rectangular shape, and is positioned to extend in a direction substantially parallel to a direction in which airflow in the airflow guiding pipe 21 flows.

This configuration allows locally increasing magnetic flux density (magnetic field density) between the convex portions 122a of the first magnet 122 and the convex portions 123a of the second magnet 123 which are positioned to face the convex portions 122a, respectively, thereby forming magnetic brushes of a two-component developer between the convex portions 122a and the convex portions 123a. Further, since the magnetic brushes of the two-component developer are generated at predetermined positions (i.e. at surfaces of the convex portions 122a and surfaces of the convex portions 123a which surfaces face the convex portions 122a, respectively) while the magnetic brushes are independent from each other, supplied airflow mainly passes through between the concave portions 122b and the concave portions 123b, and evenly hit the magnetic brushes between the convex portions 122a and the convex portions 123a. This increases reproducibility of the result of the measurement.

Figure 18:
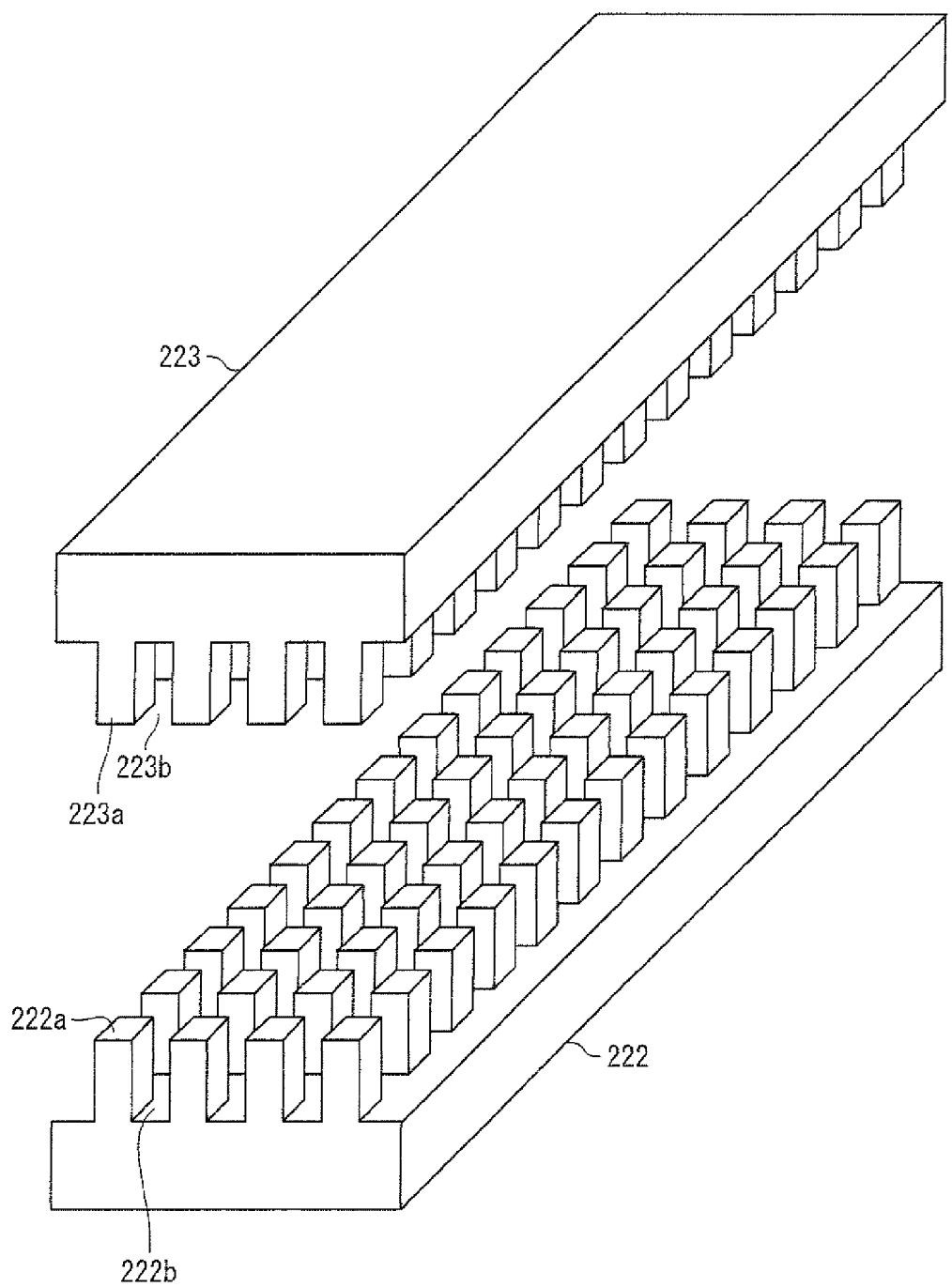
FIG. 18 is a perspective drawing showing a modification example of the first magnet and the second magnet which are shown in FIGS. 15(a) and 15(b) and which are included in the device for measuring distribution of toner adhesion.

FIG. 18 is a perspective drawing showing another modification example of the first magnet 22 and the second magnet 23 provided in the developer holding section 2 shown in FIG. 15(a). In the example shown in the drawing, a surface of a first magnet 222 which surface faces a second magnet 223 is provided with (i) a large number of convex portions (first protrusions) 222a which protrude toward the second magnet 223, and (ii) concave portions 222b (slits) each of which is positioned between adjacent ones of the convex portions 222a and which are recessed in a direction away from the second magnet 123. Further, a surface of the second magnet 223 which surface faces the first magnet 222 is provided with (i) convex portions (second protrusions) 223a which are positioned to face the convex portions 222a of the first magnet 222, respectively, and which protrude toward the first magnet 222, and (ii) concave portions (slits) 223b which are positioned to face the concave portions 222b of the first magnet 222, respectively, and which are recessed in a direction away from the first magnet 222. Further, each of the concave portions 222a and the concave portions 223b has a square column shape, and is positioned in a matrix manner where each of the concave portions 222a and the concave portions 223b is aligned in a direction (first direction) substantially parallel to a direction in which airflow in the airflow guiding pipe 21 flows and a direction (second direction) substantially perpendicular to the direction in which airflow in the airflow guiding pipe 21 flows and substantially perpendicular to a direction in which the concave portions 222a face the concave portions 223a. In the example shown in FIG. 18, each of the convex portions 222a and the convex portions 223a has a square column shape. However, the shape of the convex portions 222a and the convex portions 223a is not limited to this, and may be a circular column for example.

This configuration allows locally increasing magnetic flux density (magnetic field density) between the convex portions 222a of the first magnet 222 and the convex portions 223a of the second magnet 223 which are positioned to face the convex portions 222a, respectively, thereby forming magnetic brushes of a two-component developer between the convex portions 222a and the convex portions 223a. Further, since the magnetic brushes of the two-component developer are generated at predetermined positions (i.e. at surfaces of the convex portions 222a and surfaces of the convex portions 223a which surfaces face the convex portions 222a, respectively) while the magnetic brushes are independent from each other, supplied airflow mainly passes through between the concave portions 222b and the concave portions 223b, and evenly hit the magnetic brushes between the convex portions 222a and the convex portions 223a. This increases reproducibility of the result of the measurement.

As detailed in the above embodiments, the device of the present invention for measuring toner adhesion is a device for measuring adhesion of toner to carrier containing a magnetic component, the toner and the carrier being contained in a two-component developer, the device comprising: a developer holding section including a first magnet for holding the two-component developer by a magnetic force; an airflow supply section for supplying airflow to the two-component developer held by the first magnet; a separated toner detecting section for detecting the number of toner separated from the carrier by the airflow; and an adhesion calculating section for calculating the adhesion of the toner to the carrier or an index of the adhesion, based on wind speed of the airflow and the detected number of the separated toner. The index is not particularly limited as long as the index indicates the degree of toner adhesion. Examples of the index include: the detected number of separated toner; and a wall shear force calculated based on the wind speed at which the number of the separated toner is detected.

Further, the method of the present invention for measuring toner adhesion is a method for measuring adhesion of toner to carrier containing a magnetic component, the toner and the carrier being contained in a two-component developer, the method comprising the steps of: causing a first magnet to hold the two-component developer by a magnetic force; supplying airflow to the two-component developer held by the first magnet; detecting the number of toner separated from the carrier by the airflow; and calculating the adhesion of the toner to the carrier or an index of the adhesion, based on wind speed of the airflow and the detected number of the separated toner.

The device and the method for measuring toner adhesion can hold the two-component developer by a magnetic force generated by the first magnet, thereby holding the two-component developer in a magnetic brush-like manner. That is, the device and the method can hold the two-component developer in such a manner that the two-component developer stands perpendicularly to a surface of the first magnet which surface holds the two-component developer. Therefore, it is possible to cause the airflow to substantially evenly hit individual carrier and individual toner contained in the two-component developer. Therefore, by supplying the airflow to the two-component developer held by the first magnet, detecting the number of toner separated by the airflow, and calculating adhesion of toner to carrier or an index indicative of the toner adhesion, it is possible to measure the adhesion of toner to carrier or the index indicative of the toner adhesion with high reproducibility and exactness.

The device of the present invention may be arranged so as to further include a wind speed control section for controlling wind speed of the airflow supplied by the airflow supply section, the wind speed control section controlling the wind speed of the airflow in such a manner that the wind speed is increased monotonously, the separated toner detecting section detecting the number of the separated toner with respect to each predetermined wind speed, and the adhesion calculating section calculating distribution of the adhesion of the toner to the carrier or distribution of an index of the adhesion, based on the number of the separated toner detected with respect to each predetermined wind speed and on wind speed corresponding to the number.

With the arrangement, it is possible to measure distribution of the adhesion of toner to carrier in the two-component developer or distribution of the index indicative of the toner adhesion with high reproducibility and exactness. Therefore, even when the degree of deterioration in electrostatic property of toner contained in the two-component developer varies among individual toner or even when adhesion of toner to carrier varies among individual toner due to variations in shape etc. among individual toner, it is possible to properly evaluate the degree of deterioration of toner or property of toner based on the distribution measured as above.

Further, the device of the present invention may be arranged such that the first magnet is positioned in such a manner that a holding surface which holds the two-component developer belongs to one of a south pole and a north pole.

With the arrangement, it is possible to generate a magnetic field substantially perpendicular to the holding surface, and consequently it is possible to hold the two-component developer in such a manner that the two-component developer stands perpendicularly to the holding surface. This increases reproducibility of the result of the measurement.

Further, the device of the present invention may be arranged so as to further include a second magnet positioned to face the holding surface of the first magnet, a surface of the second magnet which surface faces the first magnet has a polarity opposite to that of the holding surface of the first magnet.

With the arrangement, it is possible to generate substantially parallel magnetic fields between the first magnet and the second magnet, and consequently it is possible to hold the two-component developer in a direction perpendicular to the holding surface. This further increases reproducibility of the result of the measurement.

Further, the device of the present invention may be arranged such that the first magnet includes a plurality of first protrusions protruding toward the second magnet, the second magnet includes a plurality of second protrusions positioned to face the first protrusions, respectively, and protruding toward the first magnet, and the first protrusions and the second protrusions form a magnetic force therebetween which holds the two-component developer. For example, the first protrusions and the second protrusions may be positioned to extend in a direction parallel to a direction in which the airflow flows. Alternatively, the first protrusions and the second protrusions may be positioned in a matrix manner where the first protrusions and the second protrusions are aligned in a first direction parallel to a direction in which the airflow flows and in a second direction perpendicular to the first direction and perpendicular to a direction in which the first protrusions face the second protrusions.

With each of the arrangements, it is possible to locally increase magnetic flux density between the first protrusions and the second protrusions, so that it is possible to generate magnetic brushes of the two-component developer between the first protrusions and the second protrusions. Further, since the magnetic brushes of the two-component developer are generated at portions of the first protrusions and portions of the second protrusions which face each other while the magnetic brushes are independent from each other, supplied airflow mainly passes through spaces between portions of the first magnet at which portions the first protrusions are not provided and portions of the second magnet at which portions the second protrusions are not provided and which portions face that portions of the first magnet, that is, passes through between the magnetic brushes generated at the portions of the first protrusions and portions of the second protrusions which face each other, so that the airflow hits the magnetic brushes evenly. This further increases reproducibility of the result of the measurement.

Further, the device of the present invention may be arranged such that the developer holding section includes an airflow guiding pipe via which the airflow supplied by the airflow supply section flows, and the airflow supplied by the airflow supply section is supplied via one end of the airflow guiding pipe, and the separated toner whose number is detected by the separated toner detecting section is exhausted via the other end of the airflow guiding pipe.

With the arrangement, it is possible to stable wind speed of the airflow supplied to the two-component developer held by the first magnet. Consequently, it is possible to increase reproducibility of the result of the measurement.

The present invention is not limited to the description of the embodiments above, but may be altered by a skilled person within the scope of the claims. An embodiment based on a proper combination of technical means disclosed in different embodiments is encompassed in the technical scope of the present invention within the scope of the claims.

INDUSTRIAL APPLICABILITY

The present invention is applicable to a device for measuring distribution of adhesion of toner to carrier in a two-component developer.

REFERENCE SIGNS LIST

1. Device for measuring distribution of toner adhesion (device for measuring toner adhesion)
2. Developer holding section
3. Airflow supply section
3a. Filter
3b. Compressor
3c. Drier
3d. Wind speed regulator
4. Separated toner detecting section
5. Calculation section
5a. Wind speed control section
5b. Bond force calculating section (adhesion calculating section)
6. Exhaust device
7a, 7b, 7c. Air pipe
8. Airflow guiding pipe
9. Exhaust pipe
21. Airflow guiding pipe
22. First magnet
23. Second magnet
C. Carrier
T1. Toner
T2. Separated toner

The invention claimed is:

1. A device for measuring adhesion of toner to carrier containing a magnetic component, the toner and the carrier being contained in a two-component developer, the device comprising:
   a developer holding section including:
      a first magnet for holding the two-component developer by a magnetic force, a holding surface of the first magnet being one of a south pole and a north pole, and
      a second magnet positioned to face the holding surface of the first magnet, a surface of the second magnet which faces the first magnet having a polarity opposite to that of the holding surface of the first magnet;
   an airflow supply section for supplying airflow to the two-component developer held by the first magnet;
   a separated toner detecting section for detecting the number of toner particles separated from the carrier by the airflow; and
   an adhesion calculating section for calculating the adhesion of the toner to the carrier or an index of the adhesion, based on wind speed of the airflow and the detected number of the separated toner particles;
   wherein the first magnet includes a plurality of first protrusions protruding toward the second magnet, and the second magnet includes a plurality of second protrusions positioned to face the first protrusions, respectively, and protruding toward the first magnet, the first protrusions and second protrusions being made of a magnetic material, and
   wherein the first protrusions and the second protrusions form a magnetic force therebetween which holds the two-component developer.

2. The device as set forth in claim 1, further comprising a wind speed control section for controlling wind speed of the airflow supplied by the airflow supply section,
   the wind speed control section controlling the wind speed of the airflow in such a manner that the wind speed is increased monotonously,
   the separated toner detecting section detecting the number of the separated toner particles with respect to each predetermined wind speed, and
   the adhesion calculating section calculating a distribution of the adhesion of the toner to the carrier or a distribution of an index of the adhesion, based on the number of the separated toner particles detected with respect to each predetermined wind speed and on wind speed corresponding to the number.

3. The device as set forth in claim 1, wherein the first protrusions and the second protrusions are positioned to extend in a direction parallel to a direction in which the airflow flows.

4. The device as set forth in claim 1, wherein the first protrusions and the second protrusions are positioned in a matrix manner where the first protrusions and the second protrusions are aligned in a first direction parallel to a direction in which the airflow flows and in a second direction perpendicular to the first direction and perpendicular to a direction in which the first protrusions face the second protrusions.

5. The device as set forth in claim 1, wherein the developer holding section includes an airflow guiding pipe via which the airflow supplied by the airflow supply section flows, and the airflow supplied by the airflow supply section is supplied via one end of the airflow guiding pipe, and the separated toner particles whose number is detected by the separated toner detecting section is exhausted via the other end of the airflow guiding pipe.

6. A method for measuring adhesion of toner to carrier containing a magnetic component, the toner and the carrier being contained in a two-component developer, the method comprising the steps of:
    causing a developer holding section to hold the two-component developer by a magnetic force, the developer holding section comprising a first magnet having a holding surface that is one of a south pole and a north pole, and a second magnet positioned to face the holding surface of the first magnet, a surface of the second magnet which faces the first magnet having a polarity opposite to that of the holding surface of the first magnet, wherein the first magnet includes a plurality of first protrusions protruding toward the second magnet, and the second magnet includes a plurality of second protrusions positioned to face the first protrusions, respectively, and protruding toward the first magnet, the first protrusions and second protrusions being made of a magnetic material, and wherein the first protrusions and the second protrusions form a magnetic force therebetween which holds the two-component developer;
    supplying airflow to the two-component developer held by the first and second magnets;
    detecting the number of toner particles separated from the carrier by the airflow; and
    calculating the adhesion of the toner to the carrier or an index of the adhesion, based on wind speed of the airflow and the detected number of the separated toner particles.

7. A device for measuring adhesion of toner to carrier containing a magnetic component, the toner and the carrier being contained in a two-component developer, the device comprising:
    a developer holding section including:
        a first magnet for holding the two-component developer by a magnetic force, a holding surface of the first magnet being of a south pole and a north pole, and
        a second magnet positioned to face the holding surface of the first magnet, a surface of the second magnet which faces the first magnet having a polarity opposite to that of the holding surface of the first magnet;
    an airflow supply section for supplying airflow to the two-component developer held by the first magnet;
    a separated toner detecting section for detecting the number of toner particles separated from the carrier by the airflow; and
    an adhesion calculating section for calculating the adhesion of the toner to the carrier or an index of the adhesion, based on wind speed of the airflow and the detected number of the separated toner particles;
    wherein the first magnet includes a plurality of first protrusions protruding toward the second magnet, and the second magnet includes a plurality of second protrusions positioned to face the first protrusions, respectively, and protruding toward the first magnet,
    wherein the first protrusions and the second protrusions form a magnetic force therebetween which holds the two-component developer, and
    wherein the first protrusions and the second protrusions are positioned in a matrix manner where the first protrusions and the second protrusions are aligned in a first direction parallel to a direction in which the airflow flows and in a second direction perpendicular to the first direction and perpendicular to a direction in which the first protrusions face the second protrusions.

8. The device as set forth in claim 7, wherein the developer holding section includes an airflow guiding pipe via which the airflow supplied by the airflow supply section flows, and wherein the airflow supplied by the airflow supply section is supplied via one end of the airflow guiding pipe, and the separated toner particles whose number is detected by the separated toner detecting section is exhausted via the other end of the airflow guiding pipe.

9. A method for measuring adhesion of toner to carrier containing a magnetic component, the toner and the carrier being contained in a two-component developer, the method comprising the steps of:
    causing a developer holding section to hold the two-component developer by a magnetic force, the developer holding section comprising a first magnet having a holding surface that is one of a south pole and a north pole, and a second magnet positioned to face the holding surface of the first magnet, a surface of the second magnet which faces the first magnet having a polarity opposite to that of the holding surface of the first magnet, wherein the first magnet includes a plurality of first protrusions protruding toward the second magnet, and the second magnet includes a plurality of second protrusions positioned to face the first protrusions, respectively, and protruding toward the first magnet, wherein the first protrusions and the second protrusions are positioned in a matrix manner where the first protrusions and the second protrusions are aligned in a first direction parallel to a direction in which an airflow flows past the protrusions and in a second direction perpendicular to the first direction and perpendicular to a direction in which the first protrusions face the second protrusions, and wherein the first protrusions and the second protrusions form a magnetic force therebetween which holds the two-component developer,
    supplying airflow to the two-component developer held by the first and second magnets;
    detecting the number of toner particles separated from the carrier by the airflow; and
    calculating the adhesion of the toner to the carrier or an index of the adhesion, based on wind speed of the airflow and the detected number of the separated toner particles.

* * * * *